United States Patent
Norisue et al.

(10) Patent No.: US 7,193,019 B2
(45) Date of Patent: Mar. 20, 2007

(54) PROCESS FOR THE PRODUCTION OF VINYL COMPOUND

(75) Inventors: Yasumasa Norisue, Tokyo (JP); Makoto Miyamoto, Tokyo (JP); Daisuke Ohno, Tokyo (JP); Kenji Ishii, Tokyo (JP); Michio Nawata, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 210 days.

(21) Appl. No.: 10/963,808

(22) Filed: Oct. 14, 2004

(65) Prior Publication Data
US 2005/0090624 A1 Apr. 28, 2005

(30) Foreign Application Priority Data
Oct. 22, 2003 (JP) ............................. 2003-362120
Jul. 20, 2004 (JP) ............................. 2004-211088

(51) Int. Cl.
*C08G 65/48* (2006.01)
(52) U.S. Cl. ..................... 525/392; 568/640; 568/641; 568/643; 568/644; 568/645; 568/646
(58) Field of Classification Search ................ 525/392; 568/640, 641, 643, 644, 645, 646
See application file for complete search history.

(56) References Cited

U.S. PATENT DOCUMENTS 4,871,831 A * 10/1989 Zweig et al. ............... 528/205

6,908,960 B2 * 6/2005 Takaya et al. ............... 524/494

FOREIGN PATENT DOCUMENTS
EP     0 310 835 A2    4/1989
EP     0 546 497 A2    6/1993

* cited by examiner

*Primary Examiner*—Rosalynd Keys
(74) *Attorney, Agent, or Firm*—Wenderoth, Lind & Ponack, L.L.P.

(57) ABSTRACT

A process for the production of a vinyl compound of the formula (1),

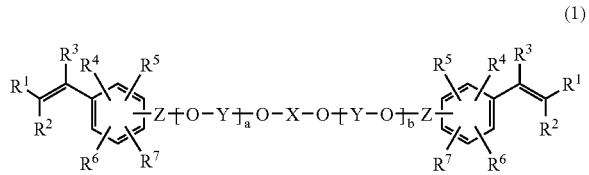

(1)

which process comprises reacting a bifunctional phenylene ether oligomer of the formula (2) with a vinylbenzyl halide in an aprotic polar solvent in the presence of an alkali metal alkoxide and then adding the reaction solution to water or a water/alcohol mixed solution to precipitate a solid

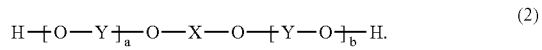

(2)

10 Claims, 3 Drawing Sheets

PROCESS FOR THE PRODUCTION OF VINYL COMPOUND

FIELD OF THE INVENTION

The present invention relates to a process for the production of a vinyl compound obtainable by reacting a bifunctional phenylene ether oligomer with a vinylbenzyl halide. More specifically, it relates to a process for the production of a vinyl compound having a remarkably low content of ionic impurities.

PRIOR ARTS OF THE INVENTION

The present inventors have found that a vinyl compound having fine curability and excellent dielectric characteristics and heat resistance can be obtained by introducing a vinyl group into a terminal of a bifunctional phenylene ether oligomer having inherited excellent dielectric characteristics and heat resistance from a polyphenylene ether resin (JP-A-2004-59644, JP-A-2004-67727).

As a method for introducing a vinyl group, there is known a synthesis method comprising reacting a phenolic hydroxyl group with a vinylbenzyl halide. For example, there are known a method using a quaternary ammonium salt such as tetra-n-butyl ammonium bromide as a phase transfer catalyst (see JP-A-6-116194, pp. 1–5, for example) and a method using an alkali metal hydroxide (see Japanese Patent No. 2656956, pp. 1–4, for example). However, it is very hard to remove a byproduct salt generated during the reaction and unreacted vinylbenzyl halide in these synthesis methods, so that a problem is that a vinyl compound obtained has a large content of ionic impurities and, for this reason, the vinyl compound can not exhibit inherent dielectric characteristics in some cases. Since it is necessary to repeat washings with pure water or the like for removing such ionic impurities, the steps becomes complicated, which causes economical disadvantages.

SUMMARY OF THE INVENTION

It is an object of the present invention to provide a process for the production of a vinyl compound which is able to be cured by heat or light and capable of giving a cured product having excellent dielectric characteristics and heat resistance and has a small content of ionic impurities, which process is advantageous in terms of production steps.

The present inventors have made diligent studies on the production process of a vinyl compound and as a result found that a vinyl compound having a less content of ionic impurities can be produced by adding a solution which have been reacted in an aprotic polar solvent in the presence of an alkali metal alkoxide to a water/alcohol mixed solution. On the basis of the above finding, the present inventors have completed the present invention.

That is, the present invention 1 provides a process for the production of a vinyl compound of the formula (1),

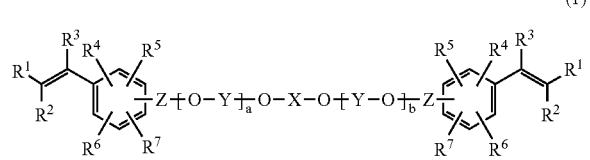

wherein:
$R^1$, $R^2$, $R^3$, $R^4$, $R^5$, $R^6$ and $R^7$ are the same or different and represent a hydrogen atom, a halogen atom, an alkyl group or a phenyl group,
—(O—X—O)— represents a moiety of the formula (3) or the formula (4),

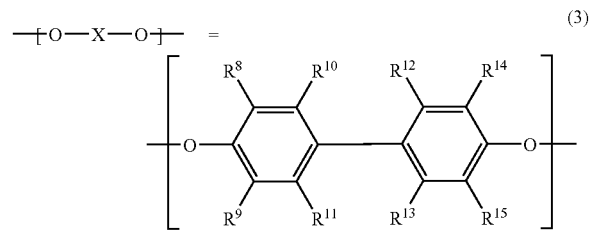

in which $R^8$, $R^9$, $R^{10}$, $R^{14}$ and $R^{15}$ are the same or different and represent a halogen atom, an alkyl group having 6 or less carbon atoms or a phenyl group and $R^{11}$, $R^{12}$ and $R^{13}$ are the same or different and represent a hydrogen atom, a halogen atom, an alkyl group having 6 or less carbon atoms or a phenyl group,

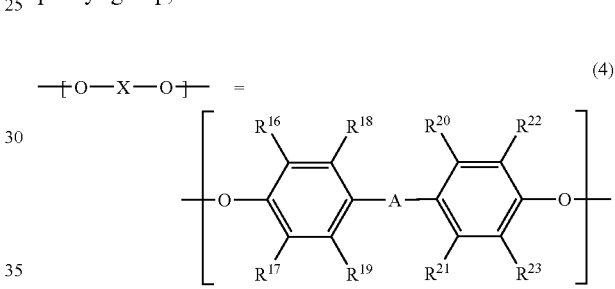

in which $R^{16}$, $R^{17}$, $R^{22}$ and $R^{23}$ are the same or different and represent a halogen atom, an alkyl group having 6 or less carbon atoms or a phenyl group, $R^{18}$, $R^{19}$, $R^{20}$ and $R^{21}$ are the same or different and represent a hydrogen atom, a halogen atom, an alkyl group having 6 or less carbon atoms or a phenyl group, and A is a linear, branched or cyclic hydrocarbon having 20 or less carbon atoms,
—(Y—O)— is a moiety of the formula (5) or a random arrangement of at least two kinds of moieties of the formula (5),

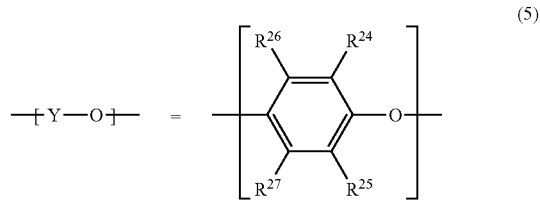

in which $R^{24}$ and $R^{25}$ are the same or different and represent a halogen atom, an alkyl group having 6 or less carbon atoms or a phenyl group and $R^{26}$ and $R^{27}$ are the same or different and represent a hydrogen atom, a halogen atom, an alkyl group having 6 or less carbon atoms or a phenyl group,
Z is an organic group having at least one carbon atom which may contain an oxygen atom, a nitrogen atom or a sulfur atom, and each of a and b is an integer of 0 to 30, provided that at least one of a and b is not 0, which process comprises reacting a bifunctional phenylene ether oligomer of the formula (2) with a vinylbenzyl halide in an aprotic polar solvent in the presence of an alkali metal alkoxide and then adding the reaction solution to a water/alcohol mixed solution to precipitate a solid,

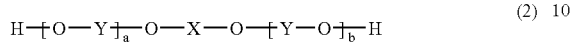
(2)

in which —(O—X—O)—, —(Y—O)—, a and b are as defined in the formula (1).

Further, the present invention 2 provides a process for the production of a vinyl compound of the formula (1),

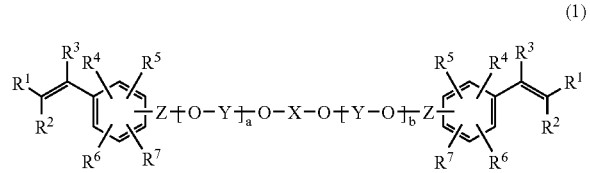
(1)

wherein:

$R^1$, $R^2$, $R^3$, $R^4$, $R^5$, $R^6$ and $R^7$ are the same or different and represent a hydrogen atom, a halogen atom, an alkyl group or a phenyl group, —(O—X—O)— represents a moiety of the formula (3) or the formula (4),

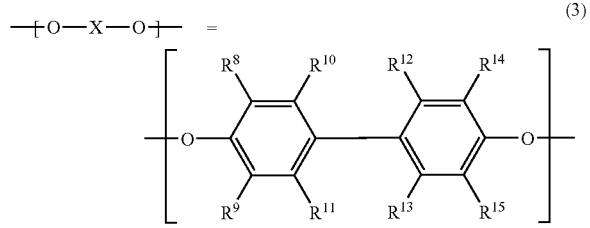
(3)

in which $R^8$, $R^9$, $R^{10}$, $R^{14}$ and $R^{15}$ are the same or different and represent a halogen atom, an alkyl group having 6 or less carbon atoms or a phenyl group and $R^{11}$, $R^{12}$ and $R^{13}$ are the same or different and represent a hydrogen atom, a halogen atom, an alkyl group having 6 or less carbon atoms or a phenyl group,

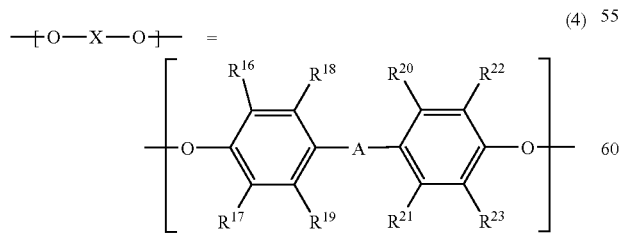
(4)

in which $R^{16}$, $R^{17}$, $R^{22}$ and $R^{23}$ are the same or different and represent a halogen atom, an alkyl group having 6 or less carbon atoms or a phenyl group, $R^{18}$, $R^{19}$, $R^{20}$ and $R^{21}$ are the same or different and represent a hydrogen atom, a halogen atom, an alkyl group having 6 or less carbon atoms or a phenyl group, and A is a linear, branched or cyclic hydrocarbon having 20 or less carbon atoms, —(Y—O)— is a moiety of the formula (5) or a random arrangement of at least two kinds of moieties of the formula (5),

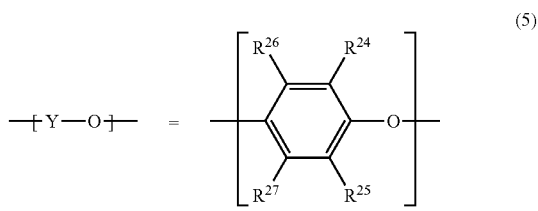
(5)

in which $R^{24}$ and $R^{25}$ are the same or different and represent a halogen atom, an alkyl group having 6 or less carbon atoms or a phenyl group and $R^{26}$ and $R^{27}$ are the same or different and represent a hydrogen atom, a halogen atom, an alkyl group having 6 or less carbon atoms or a phenyl group, Z is an organic group having at least one carbon atom which may contain an oxygen atom, a nitrogen atom or a sulfur atom, and each of a and b is an integer of 0 to 30, provided that at least one of a and b is not 0, which process comprises adding an aprotic polar solvent having a boiling point higher than that of a reaction solvent of a reaction solution (a) which has synthesized a bifunctional phenylene ether oligomer of the formula (2) to the reaction solution (a), replacing the reaction solvent of the reaction solution (a) with the aprotic polar solvent by distillation to obtain a bifunctional phenylene ether oligomer solution, reacting the bifunctional phenylene ether oligomer solution with a vinylbenzyl halide in the presence of an alkali metal alkoxide to synthesize the vinyl compound of the formula (1) and obtain a reaction solution (b), neutralizing the reaction solution (b) with an acid substance and then adding the neutralized solution to water or a water/alcohol mixed solution, to precipitate a solid,

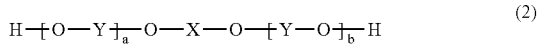
(2)

in which —(O—X—O)—, —(Y—O)—, a and b are as defined in the formula (1).

DETAILED DESCRIPTION OF THE INVENTION

Figure 1:
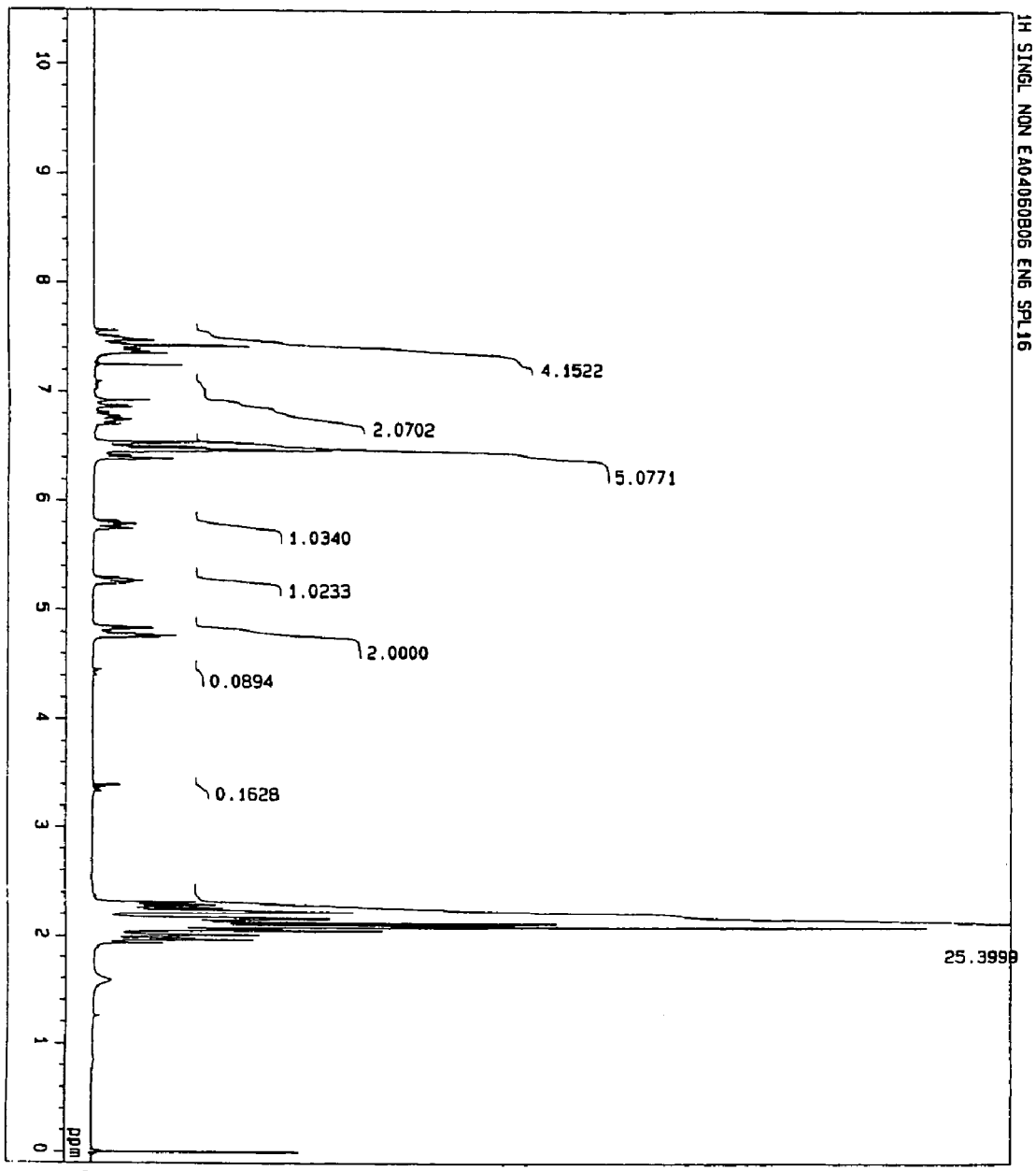
FIG. 1 shows the $^1$H-NMR chart of a vinyl compound in Example 1.

The process for producing the vinyl compound of the formula (1), provided by the present invention 1, comprises reacting a bifunctional phenylene ether oligomer of the formula (2) with a vinylbenzyl halide in an aprotic polar solvent in the presence of alkali metal alkoxide and adding the resultant reaction solution to a water/alcohol mixed solution.

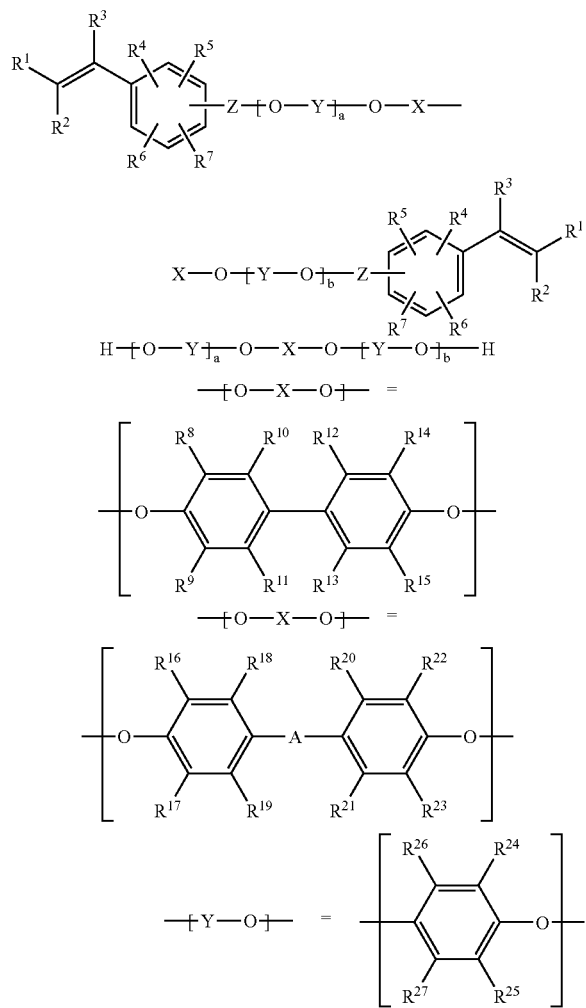

wherein $R^1$, $R^2$, $R^3$, $R^4$, $R^5$, $R^6$ and $R^7$ are the same or different and represent a hydrogen atom, a halogen atom, an alkyl group or a phenyl group, —(O—X—O)— represents a moiety of the formula (3) or the formula (4) (in which $R^8$, $R^9$, $R^{10}$, $R^{14}$, $R^{15}$ $R^{16}$, $R^{17}$, $R^{22}$ and $R^{23}$ are the same or different and represent a halogen atom, an alkyl group having 6 or less carbon atoms or a phenyl group, $R^{11}$, $R^{12}$, $R^{13}$, $R^{18}$, $R^{19}$, $R^{20}$ and $R^{21}$ are the same or different and represent a hydrogen atom, a halogen atom, an alkyl group having 6 or less carbon atoms or a phenyl group and A is a linear, branched or cyclic hydrocarbon having 20 or less carbon atoms), —(Y—O)— is a moiety of the formula (5) or a random arrangement of at least two kinds of moieties of the formula (5) (in which $R^{24}$ and $R^{25}$ are the same or different and represent a halogen atom, an alkyl group having 6 or less carbon atoms or a phenyl group and $R^{26}$ and $R^{27}$ are the same or different and represent a hydrogen atom, a halogen atom, an alkyl group having 6 or less carbon atoms or a phenyl group), Z is an organic group having at least one carbon atom which may contain an oxygen atom, a nitrogen atom or a sulfur atom, and each of a and b is an integer of 0 to 30, provided that at least one of a and b is not 0.

The bifunctional phenylene ether oligomer used in the present inventions 1 and 2 is not specially limited so long as it has a structure represented by the formula (2). Preferably, it is a bifunctional phenylene ether oligomer in which $R^8$, $R^9$, $R^{10}$, $R^{14}$, $R^{15}$, $R^{16}$, $R^{17}$, $R^{22}$ and $R^{23}$ in —(O—X—O)— represented by the formula (3) or the formula (4) are alkyl groups having 3 or less carbon atoms, $R^{11}$, $R^{12}$, $R^{13}$, $R^{18}$, $R^{19}$, $R^{20}$ and $R^{21}$ are hydrogen atoms or alkyl groups having 3 or less carbon atoms, $R^{24}$ and $R^{25}$ in —(Y—O)— represented by the formula (5) are alkyl groups having 3 or less carbon atoms and $R^{26}$ and $R^{27}$ are hydrogen atoms or alkyl groups having 3 or less carbon atoms. Particularly preferably, it is a bifunctional phenylene ether oligomer in which $R^8$, $R^9$, $R^{10}$, $R^{14}$, $R^{15}$, $R^{16}$, $R^{17}$, $R^{22}$ and $R^{23}$ in represented by the formula (3) or the formula (4) are methyl groups and —(Y—O)— represented by the formula (5) is represented by the formula (6) or the formula (7).

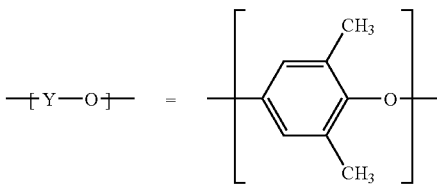

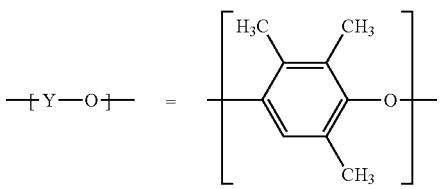

The bifunctional phenylene ether oligomer of the formula (2) used in the present inventions 1 and 2 is produced by, for example, a method in which a bivalent phenol and a monovalent phenol are copolymerized in a reaction solvent in the presence of a catalyst, disclosed in JP-A-2004-115619, or the like. The above reaction solvent includes aromatic hydrocarbon solvents such as toluene, benzene, xylene, etc., halogenated hydrocarbon solvents such as methylene chloride, chloroform, etc., and a mixed solvent of at least one of these solvents and a ketone solvent or an alcohol solvent. As for the reaction conditions, the reaction is generally carried out at 30–50° C. for about 1–5 hours, and the resultant reaction solution is washed, concentrated and dried, to obtain the bifunctional phenylene ether oligomer. The reaction solution (a) used in the present invention 2 is obtained by non-execution of concentration and drying.

The vinylbenzyl halide used in the present inventions 1 and 2 is not specially limited. Preferable examples thereof include m-vinylbenzyl chloride, p-vinylbenzyl chloride, and a mixture of these; and m-vinylbenzyl bromide, p-vinylbenzyl bromide and a mixture of these. These vinylbenzyl halides may be used alone or in combination as required. The amount of the vinylbenzyl halide used in the present invention is 0.9–4.0 mol, more preferably 1.0–2.0 mol, per 1.0 mol of a phenolic hydroxyl group of the bifunctional phenylene ether oligomer. When the amount of the vinyl benzyl halide is small, the residue of unreacted phenolic hydroxyl group increases, which results in a decrease in the dielectric characteristics of a cured product. When the amount of the vinyl benzyl halide is large, only the amount of unreacted vinylbenzyl halide increases while the reaction rate does not change, which decreases the dielectric characteristics of a cured product and causes economical disadvantages.

The alkali metal alkoxide used in the present inventions 1 and 2 is not specially limited. Preferable examples thereof include lithium methoxide, sodium methoxide, potassium methoxide, lithium ethoxide, sodium ethoxide and potassium ethoxide. These alkali metal alkoxides may be used alone or in combination. The amount of the alkali metal alkoxide used in the present invention is 0.9–4.8 mol, more preferably 1.0–2.4 mol, per 1.0 mol of a phenolic hydroxyl group of the bifunctional phenylene ether oligomer and concurrently 1.0–1.2 mol per 1.0 mol of the vinylbenzyl halide. The alkali metal alkoxide reacts with the vinylbenzyl halide, as shown in the reaction formula (8), to form an ether. Therefore, when the alkali metal alkoxide is used in an amount at least equimolar to the amount of the vinylbenzyl halide, there can be produced a vinyl compound having an extremely small content of remaining unreacted vinylbenzyl halide which becomes ionic impurities.

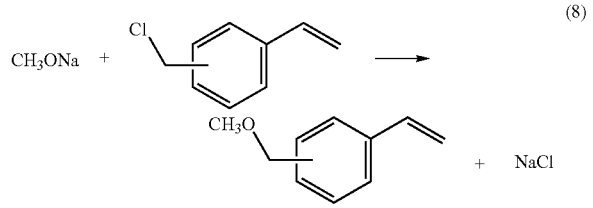

(8)

The aprotic polar solvent used for a reaction solvent in the present invention 1 is not specially limited. Preferable examples thereof include acetone, methyl ethyl ketone, methyl isobutyl ketone, N,N-dimethylformamide, N,N-dimethylacetamide and N-methyl-2-pvrrolidone. These aprotic polar solvents may be used alone or in combination as required. Further, an aprotic nonpolar solvent may be used in combination with the aprotic polar solvent. Preferable examples of the aprotic nonpolar solvent include tetrahydrofuran, chlorobenzene, 1,4-dioxane, benzene, toluene, xylene, ethyl benzene or mesitylene. These reaction solvents may be used in arbitrary amounts, while the aprotic polar solvent is preferably used in an amount of 100–2,000 parts by weight per 100 parts by weight of the bifunctional phenylene ether oligomer of the formula (2) and the aprotic nonpolar solvent is preferably used in an amount of 0–500 parts by weight per 100 parts by weight of the bifunctional phenylene ether oligomer of the formula (2).

The reaction time of the bifunctional phenylene ether oligomer and the vinylbenzyl halide in the present invention 1 and the present invention 2 is arbitrary and it may be 30 minutes to 30 hours, preferably 1 hour to 10 hours. Further, the reaction temperature is not specially limited, and it is 0–100° C., preferably 10–60° C.

In the production processes of the present inventions 1 and 2, after the reaction, the reaction solution is directly added to water or a water/alcohol mixed solution without the step of washing an organic layer with pure water or the like, thereby precipitating a solid. Generally, when an organic solution of an oligomer dissolved is washed with water, separating an aqueous layer and an organic layer is difficult, so that a liquid-separation washing step takes a very long time. Further, even when the liquid-separation washing is carried out with water, it is also very difficult to completely remove a byproduct salt generated in the reaction. The production processes of the present inventions 1 and 2 can omit such a complicated liquid-separation washing step and can dissolve and remove a byproduct salt generated in the reaction by carrying out solidification using water or a water/alcohol mixed solution. Furthermore, since the reaction is carried out in a water-soluble aprotic polar solvent, water can be used as a poor solvent for the solidification so that such a complicated liquid-separation washing step can be omitted. Moreover, a reaction material is added to water or water/alcohol mixed solution to carry out solidification, and the solid obtained is washed with water, an alcohol or a water/alcohol mixed solution, whereby a byproduct salt generated in the reaction can be dissolved and removed.

The alcohol used in the water/alcohol mixed solution used for the solidification in the present invention 1 is not specially limited so long as it is compatible with water. Preferable examples thereof include methanol, ethanol, n-propanol or isopropanol. Of these, methanol or ethanol is particularly preferable. The mixing ratio of the alcohol to water is preferably 40–95% by weight, more preferably 50–90% by weight. When the amount of the alcohol is smaller than 40% by weight, a vinyl compound obtained becomes starch-syrup-like and is therefore difficult to handle. When it is more than 95% by weight, it is impossible to sufficiently dissolve and remove a byproduct salt contained in the reaction solution, generated in the reaction, since the water content is small. According to the production processes of the present inventions, there can be efficiently produced a vinyl compound having an extremely small content of ionic impurities and a extremely small content of remaining alkali metal ions.

In the present invention 2, the aprotic polar solvent to be added to the reaction solution (a) which has synthesized a bifunctional phenylene ether oligomer is not specially limited so long as it is an aprotic polar solvent which has a boiling point higher than that of reaction solvent used for the synthesis of the bifunctional phenylene ether oligomer. Preferable examples thereof include N,N-dimethylformamide, N,N-dimethylacetamide and Nmethyl-2-pyrrolidone. These aprotic polar solvents may be used alone or in combination as required. The aprotic polar solvent may be used in an arbitrary amount. The amount thereof is preferably 100–2,000 parts by weight, more preferably 200–600 parts by weight, per 100 parts by weight of the bifunctional phenylene ether oligomer.

The above aprotic polar solvent is added to the reaction solution (a) in which the bifunctional phenylene ether oligomer has been synthesized, and distillation is carried out to replace a reaction solvent of the reaction solution (a) with the aprotic polar solvent, thereby obtaining a bifunctional phenylene ether oligomer solution. Such solvents replacement can be carried out by a continuous or batch distillation under a normal pressure or a reduced pressure. The temperature of a distillation still may be an arbitrary temperature, while it is preferably 80° C. to 240° C. The content of the bifunctional phenylene ether oligomer reaction solvent in the bifunctional phenylene ether oligomer solution after the solvents replacement is preferably 5% by weight or less, more preferably 2% by weight or less.

The bifunctional phenylene ether oligomer solution, which contains the aprotic polar solvent as a solvent due to the above solvents replacement, is reacted with a vinylbenzyl halide in the presence of an alkali metal alkoxide, to synthesize a vinyl compound represented by the formula (1) and obtain a reaction solution (b). The reaction time therefor is arbitrary, and it is 30 minutes to 30 hours, preferably 1 hour to 10 hours. Further, the reaction temperature is not specially limited, and it is 0–100° C., preferably 10–60° C. The present production process can remove a nonpolar solvent, etc., which decreases the synthesis reaction rate of the vinyl compound, thanks to the solvents replacement, so that the present production process has a feature that the reaction proceeds promptly.

In contrast, when a vinyl compound is synthesized in a state where the solvent used for the synthesis of the bifunctional phenylene ether oligomer remains in a large amount without carrying out the solvents replacement, it is difficult to obtain the vinyl compound as a solid since the vinyl compound is apt to become a viscous material when adding the reaction solution to water or water/alcohol mixed solution for separating the vinyl compound as a solid. Further, it is possible to prepare a solid by a method in which the reaction solution (a) of the bifunctional phenylene ether oligomer is added to a poor solvent or the like in advance and then synthesize a vinyl compound from the above solid as a raw material in an aprotic polar solvent. However, the steps are complicated so that this process is not economical.

In the production process of the present invention 2, it is preferred to remove remaining alkali metal ions by neutralizing the reaction solution (b) with an acid substance at the time when the synthesis reaction of the vinyl compound of the formula (1) is terminated. The acid substance may be selected from the group consisting of phosphoric acid, sulfuric acid, hydrochloric acid, aromatic sulfonic acid and aromatic carboxylic acid. These acid substances may be used alone or in combination. The amount of the acid substance to be used is not specially limited so long as it is sufficient for neutralizing an excess alkali of the reaction solution (b). The acid substance is preferably added in such an amount to adjust the pH of the reaction solution to 6.0–8.0, more preferably 6.5–7.5.

According to the production processes of the present invention, there can be produced a vinyl compound having an extremely small content of ionic impurities and an extremely small content of remaining alkali metals. The production processes of the present invention do not include a washing liquid-separation step which is a very complicated step so that the production processes of the present invention are economically advantageous processes. Furthermore, a cured product obtained by thermally curing the above vinyl compound has remarkable excellent dielectric characteristics so that it can be advantageously used as a high-frequency support material in electric and electronic material fields.

EXAMPLES

The present invention will be concretely explained with reference to Examples and Comparative Examples hereinafter, while the present invention shall not be specially limited to these Examples. Further, measurement methods are as follows.

A number average molecular weight and a weight average molecular weight were measured according to the gel permeation chromatography (GPC) method. Data processing was carried out according to the GPC curve and molecular weight calibration curve of a sample. The molecular weight calibration curve was obtained by making an approximation of a relation between the molecular weight of a standard polystyrene and the dissolution time thereof with the following equation, $$\text{Log } M = A_0 X^3 + A_1 X^2 + A_2 X + A_3 + A_4/X^2$$

wherein M a molecular weight, X: an elution time—19 (minute), and A: a coefficient.

Figure 2:
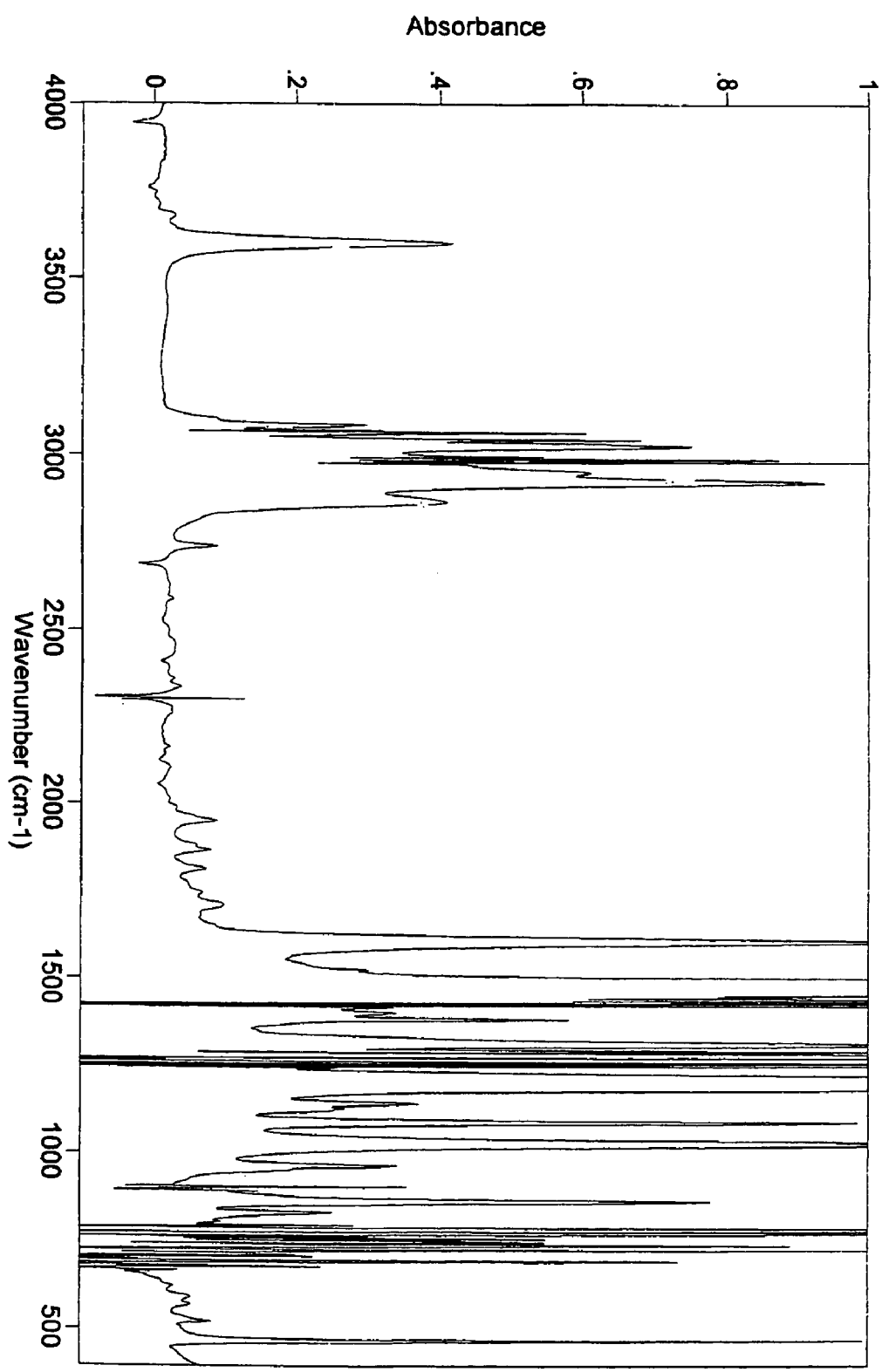
FIG. 2 shows the IR chart of a bifunctional phenylene ether oligomer in Referential Example 1.

2) A hydroxyl group equivalent was determined from an absorption intensity at 3,600 cm-1 in an IR analysis (solution cell method; cell thickness=1 mm) using 2,6-dimethyiphenol as a standard reference material and using dry dichloromethane as a solvent (FIG. 2).

Figure 3:
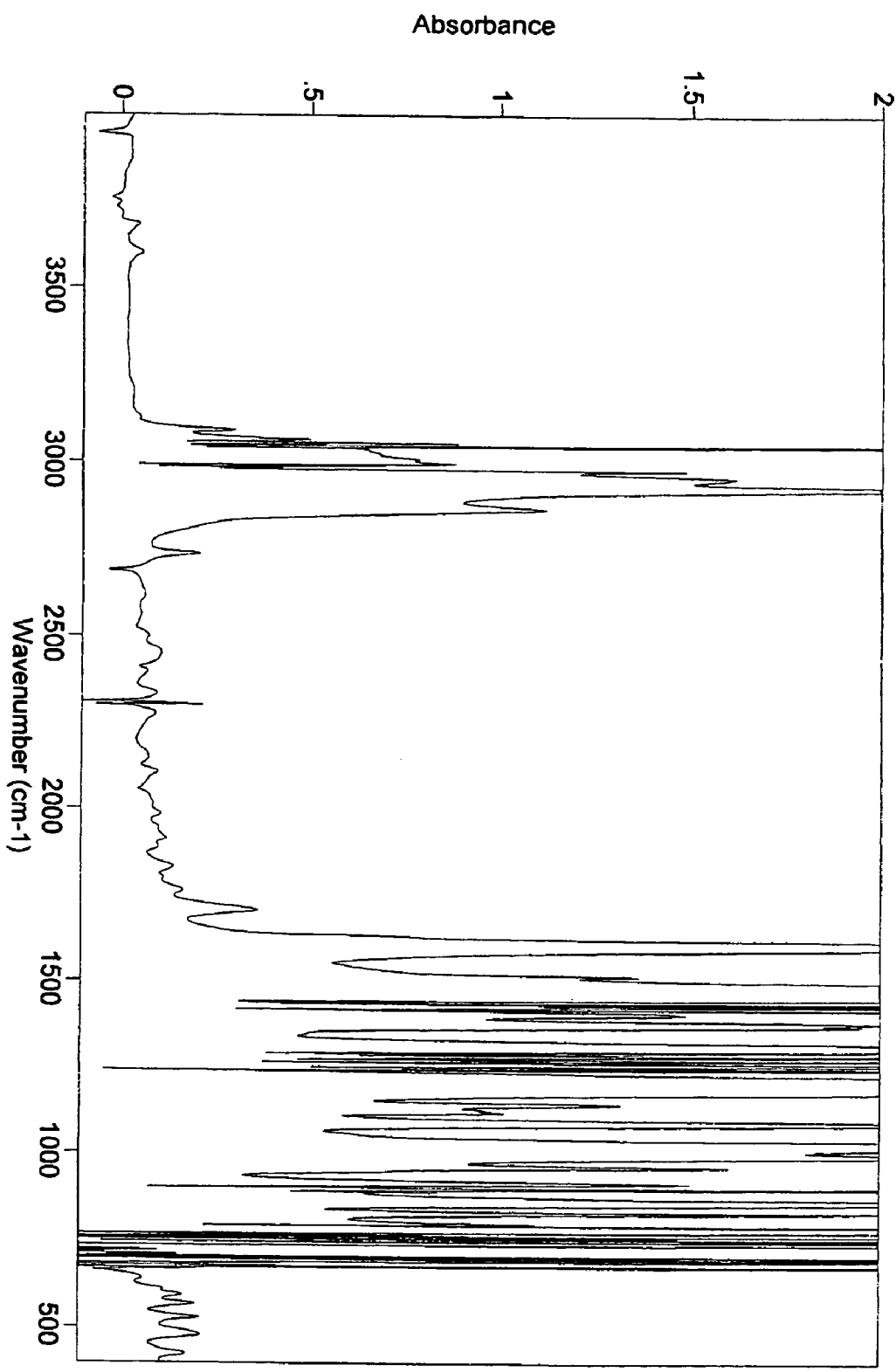
FIG. 3 shows the IR chart of a vinyl compound in Example 1.

3) A vinyl compound was confirmed by a peak of vinylbenzyl ether in a $^1$H-NMR analysis (FIG. 1). Further, it was confirmed according to an IR analysis that the peak (FIG. 2) of a phenolic hydroxyl group of a bifunctional phenylene ether oligomer disappeared in the vinyl compound (FIG. 3).

4) The amount of a hydrolysable halogen was measured as follows. A vinyl compound was dissolved in dioxane, 3 N potassium hydroxide ethanol solution was added thereto, and the mixture was stirred under heat for 30 minutes under a reflux state. The amount of a halogen which had been eliminated during the above stirring was quantified by titration with a silver nitrate aqueous solution. The amount was represented by weight fraction.

5) The dielectric constant and dielectric loss tangent of a cured product were obtained by a cavity resonance perturbation method.

Referential Example 1

Synthesis of a Bifunctional Phenylene Ether Oligomer

A longitudinally long reactor having a volume of 12 liters and equipped with a stirrer, a thermometer, an air-introducing tube and baffle plates was charged with 3.88 g (17.4 mmol) of $CuBr_2$, 0.75 g (4.4 mmol) of N,N'-di-t-butylethylenediamine, 28.04 g (277.6 mmol) of n-butyldimethylamine and 2,600 g of toluene. The components were stirred at a reaction temperature of 40° C. A mixed solution was obtained by dissolving 129.32 g (0.48 mol) of 2,2'-,3,3'-,5,5'-hexamethyl-(1,1'-biphenyl)-4,4'-diol, 292.19 g (2.40 mol) of 2,6-dimethylphenol, 0.51 g (2.9 mmol) of N,N'-di-t-butylethylenediamine and 10.90 g (108.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 19.89 g (52.3 mmol) of tetrasodium ethylenediamine tetraacetate was dissolved was added to the stirred mixture to terminate the reaction. An aqueous layer and an organic layer were separated. Then, the organic layer was washed with 1.0N hydrochloric acid aqueous solution and then washed with pure water. The thus-obtained solution was concentrated by an evaporator, to obtain 835.20 g of a 50 wt % toluene solution of a bifunctional phenylene ether oligomer. The bifunctional phenylene ether oligomer had a number average molecular weight of 940, a weight average molecular weight of 1,490 and a hydroxyl group equivalent of 470.

Referential Example 2

Synthesis of a Bifunctional Phenylene Ether Oligomer

A longitudinally long reactor having a volume of 12 liters and equipped with a stirrer, a thermometer, an air-introducing tube and baffle plates was charged with 3.88 g (17.4 mmol) of CuBr$_2$, 0.75 g (4.4 mmol) of N,N'-di-t-butylethylenediamine, 28.04 g (277.6 mmol) of n-butyldimethylamine and 2,600 g of toluene. The components were stirred at a reaction temperature of 40° C. A mixed solution was obtained by dissolving 129.32 g (0.48 mol) of 2,2'-,3,3'-,5,5'-hexamethyl-(1,1'-biphenyl)-4,4'-diol, 292.19 g (2.40 mol) of 2,6-dimethylphenol, 0.51 g (2.9 mmol) of N,N'-di-t-butylethylenediamine and 10.90 g (108.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 19.89 g (52.3 mmol) of tetrasodium ethylenediamine tetraacetate was dissolved was added to the stirred mixture to terminate the reaction. An aqueous layer and an organic layer were separated. Then, the organic layer was washed with 1.0N hydrochloric acid aqueous solution and then washed with pure water. The thus-obtained solution was concentrated by an evaporator and then dried under vacuum at 120° C., to obtain 418.30 g of a bifunctional phenylene ether oligomer. The bifunctional phenylene ether oligomer had a number average molecular weight of 970, a weight average molecular weight of 1,520 and a hydroxyl group equivalent of 480.

Example 1

A reactor equipped with a stirrer, a thermometer and a reflux tube was charged with 200.0 g (OH equivalent 0.21 mol) of the 50 wt % toluene solution of the bifunctional phenylene ether oligomer obtained in Referential Example 1, 35.7 g (0.23 mol) g of chloromethyl styrene (trade name CMS-P; supplied by Seimi Chemical Co., Ltd.) and 300 g of N,N-dimethylformamide, and the mixture was stirred under heat at 50° C. 44.4 g (0.23 mol) of a methanol solution (concentration: 28.5 wt %) of sodium methoxide was dropwise added thereto while maintaining the reaction temperature at 50° C. and the mixture was stirred for 2.5 hours. Further, 4.0 g (0.02 mol) of a methanol solution (same) of sodium methoxide was dropwise added, and the mixture was stirred for 2.5 hours. The reaction solution was dropwise added to 83 wt % methanol water, to obtain a solid. The solid was separated by filtration, and the solid was washed with 50 wt % methanol water and then methanol. Then, the washed solid was dried under a reduced pressure, to obtain 119 g of an intended vinyl compound. The vinyl compound had a number average molecular weight of 1,200, a weight average molecular weight of 1,740 and a hydrolysable halogen amount of 80 ppm. Unreacted chloromethyl styrene was not detected. The vinyl compound was molten, degassed and molded at 150° C. and cured at 200° C. for 3 hours to obtain a cured product. The cured product was measured for dielectric characteristics. Table 1 shows results thereof.

Example 2

A reactor equipped with a stirrer, a thermometer and a reflux tube was charged with 200.0 g (OH equivalent 0.21 mol) of the 50 wt % toluene solution of the bifunctional phenylene ether oligomer obtained in Referential Example 1, 35.7 g (0.23 mol) g of chloromethyl styrene (CMS-P) and 400 g of N,N-dimethylformamide, and the mixture was stirred under heat at 50° C. 44.4 g (0.23 mol) of a methanol solution (concentration: 28.5 wt %) of sodium methoxide was dropwise added thereto while maintaining the reaction temperature at 50° C. and the mixture was stirred for 2.5 hours. Further, 4.0 g (0.02 mol) of a methanol solution (same) of sodium methoxide was dropwise added, and the mixture was stirred for 2.5 hours. The reaction solution was dropwise added to 81 wt % methanol water, to obtain a solid. The solid was separated by filtration, and the solid was washed with 50 wt % methanol water and then methanol. Then, the washed solid was dried under a reduced pressure, to obtain 116 g of an intended vinyl compound. The vinyl compound had a number average molecular weight of 1,220, a weight average molecular weight of 1,770 and a hydrolysable halogen amount of 65 ppm. Unreacted chloromethyl styrene was not detected. The vinyl compound was molten, degassed and molded at 150° C. and cured at 200° C. for 3 hours to obtain a cured product. The cured product was measured for dielectric characteristics. Table 1 shows results thereof.

Example 3

A reactor equipped with a stirrer, a thermometer and a reflux tube was charged with 100.0 g (0.21 mol) of the bifunctional phenylene ether oligomer obtained in Referential Example 2, 35.0 g (0.23 mol) g of chloromethyl styrene (CMS-P) and 300 g of N,N-dimethylformamide, and the mixture was stirred under heat at 50° C. 43.4 g (0.23 mol) of a methanol solution (concentration: 28.5 wt %) of sodium methoxide was dropwise added thereto while maintaining the reaction temperature at 50° C. and the mixture was stirred for 2.5 hours. Further, 3.9 g (0.02 mol) of a methanol solution (same) of sodium methoxide was dropwise added, and the mixture was stirred for 2.5 hours. The reaction solution was dropwise added to 83 wt % methanol water, to obtain a solid. The solid was separated by filtration, and the solid was washed with 50 wt % methanol water and then methanol. Then, the washed solid was dried under a reduced pressure, to obtain 122 g of an intended vinyl compound. The vinyl compound had a number average molecular weight of 1,180, a weight average molecular weight of 1,710 and a hydrolysable halogen amount of 50 ppm. Unreacted chloromethyl styrene was not detected. The vinyl compound was molten, degassed and molded at 150° C. and cured at 200° C. for 3 hours to obtain a cured product. The cured product was measured for dielectric characteristics. Table 1 shows results thereof.

Example 4

A reactor equipped with a stirrer, a thermometer and a reflux tube was charged with 100.0 g (OH equivalent 0.21 mol) of the bifunctional phenylene ether oligomer obtained in Referential Example 2, 35.0 g (0.23 mol) g of chloromethyl styrene (CMS-P) and 300 g of N,N-dimethylformamide, and the mixture was stirred under heat at 50° C. 87.1 g (0.23 mol) of an ethanol solution (concentration: 20.3 wt %) of sodium ethoxide was dropwise added thereto while maintaining the reaction temperature at 50° C. and the mixture was stirred for 3 hours. Further, 7.9 g (0.02 mol) of an ethanol solution (same) of sodium ethoxide was dropwise added, and the mixture was stirred for 3 hours. The reaction solution was dropwise added to 75 wt % ethanol water, to obtain a solid. The solid was separated by filtration, and the solid was washed with 50 wt % ethanol water and then ethanol. Then, the washed solid was dried under a reduced pressure, to obtain 115 g of an intended vinyl compound. The vinyl compound had a number average molecular weight of 1,230, a weight average molecular weight of 1,790 and a hydrolysable halogen amount of 90 ppm. Unreacted chloromethyl styrene was not detected. The vinyl compound was molten, degassed and molded at 150° C. and cured at 200° C. for 3 hours to obtain a cured product. The cured product was measured for dielectric characteristics. Table 1 shows results thereof.

Comparative Example 1

A reactor equipped with a stirrer, a thermometer and a reflux tube was charged with 200.0 g (0.21 mol) of the 50 wt % toluene solution of the bifunctional phenylene ether oligomer obtained in Referential Example 1, 10.2 g (0.26 mol) g of sodium hydroxide and 361 g of N,N-dimethylformamide, and the mixture was stirred under heat at 40° C. for 4 hours. A mixed solution of 39.0 g (0.26 mol) of chloromethyl styrene (CMS-P) and 39.0 g of N,N-dimethylformamide was dropwise added thereto while maintaining the reaction temperature at 40° C. and the mixture was further stirred for 20 hours. The reaction solution was dropwise added to 83 wt % methanol water, to obtain a solid. The solid was separated by filtration, and the solid was washed with 50 wt % methanol water and then methanol. Then, the washed solid was dried under a reduced pressure, to obtain 120 g of an intended vinyl compound. The vinyl compound had a number average molecular weight of 1,250, a weight average molecular weight of 1,830 and a hydrolysable halogen amount of 900 ppm. It was confirmed that the unreacted chloromethyl styrene remained in an amount of 0.4%. The vinyl compound was molten, degassed and molded at 150° C. and cured at 200° C. for 3 hours to obtain a cured product. The cured product was measured for dielectric characteristics. Table 1 shows results thereof.

Comparative Example 2

A reactor equipped with a stirrer, a thermometer and a reflux tube was charged with 100.0 g (0.21 mol) of the bifunctional phenylene ether oligomer obtained in Referential Example 2, 35.0 g (0.23 mol) g of chloromethyl styrene (CMS-P), 38.9 g (0.29 mol) of 30% sodium hydroxide aqueous solution, 6.5 g (0.02 mol) of tetra-n-butylammonium bromide, 400 g of dichloromethane and 300 g of pure water, and the mixture was stirred under heat at 35° C. for 19 hours. An organic layer and an aqueous layer were separated. The organic layer was washed with 1N hydrochloric acid aqueous solution and then washed with pure water. The thus-obtained solution was dropwise added to methanol to obtain a solid. The solid was separated by filtration and washed with methanol. Then, the washed solid was dried under a reduced pressure to obtain 112 g of an intended vinyl compound. The vinyl compound had a number average molecular weight of 1,310, a weight average molecular weight of 1,980 and a hydrolysable halogen amount of 2,400 ppm. It was confirmed that the unreacted chloromethyl styrene remained in an amount of 0.8%. The vinyl compound was molten, degassed and molded at 150° C. and cured at 200° C. for 3 hours to obtain a cured product. The cured product was measured for dielectric characteristics. Table 1 shows results thereof.

TABLE 1

| | | Ex. 1 | Ex. 2 | Ex. 3 | Ex. 4 | CEx. 1 | CEx. 2 |
|---|---|---|---|---|---|---|---|
| | Solvent | DMF Toluene | DMF Toluene | DMF | DMAC | DMF Toluene | Dichloromethane Water |
| | Base | MeONa | MeONa | MeONa | EtONa | NaOH | NaOH/tetra-n-butyl ammonium bromide |
| | Reaction Time [hr] | 5 | 5 | 5 | 6 | 20 | 19 |
| | Mn | 1,200 | 1,220 | 1,180 | 1,230 | 1,250 | 1,310 |
| | Mw | 1,740 | 1,770 | 1,710 | 1,790 | 1,830 | 1,980 |
| | CMS-P remain [%] | 0 | 0 | 0 | 0 | 0.4 | 0.8 |
| | Hydrolysable halogen [ppm] | 80 | 65 | 50 | 90 | 900 | 2,400 |
| Cured product | Dielectric constant (10 GHz) | 2.38 | 2.38 | 2.36 | 2.39 | 2.43 | 2.45 |
| | Dielectric loss tangent (10 GHz) | 0.0027 | 0.0026 | 0.0025 | 0.0028 | 0.0038 | 0.0045 |

EX.: Example,
CEx.: Comparative Example
DMF: N,N-dimethylformamide
DMAC: N,N-dimethylacetamide In the following Examples and Comparative Examples, quantitative analysis of a solution and analysis of sodium were carried out in addition to the above measurement items.

6) The quantitative analysis of a solution was carried out by a gas chromatography (GC-14 A; supplied by SHIMADZU CORPORATION) with a glass column PEG-20M (Tinol science).

7) The analysis of Na was carried out using a fluorescent X-ray analyzer RIX3000 (supplied by Rigaku Corporation).

Referential Example 3

A longitudinally long reactor having a volume of 12 liters and equipped with a stirrer, a thermometer, an air-introducing tube and baffle plates was charged with 2.78 g (12.4 mmol) of $CuBr_2$, 0.54 g (3.2 mmol) of N,N'-di-t-butylethylenediamine, 16.70 g (165.0 mmol) of n-butyldimethylamine and 2,600 g of toluene. The components were stirred at a reaction temperature of 40° C. A mixed solution was obtained by dissolving 129.32 g (0.48 mol) of 2,2'-,3,3'-,5,5'-hexamethyl-(1,1'-biphenyl)-4,4'-diol (to be referred to as "HMBP" hereinafter), 175.31 g (1.44 mol) of 2,6-dimethylphenol, 0.36 g (2.1 mmol) of N,N'-di-t-butylethylenediamine and 11.13 g (110.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 16.88 g (37.3 mmol) of tetrasodium ethylenediamine tetraacetate was dissolved was added to the stirred mixture to terminate the reaction. An aqueous layer and an organic layer were separated. Then, the organic layer was washed with pure water, to obtain 2,839.24 g of a reaction solution (A) of a bifunctional phenylene ether oligomer. The bifunctional phenylene ether oligomer had a number average molecular weight of 650, a weight average molecular weight of 1,040 and a hydroxyl group equivalent of 325.

Referential Example 4

A longitudinally long reactor having a volume of 12 liters and equipped with a stirrer, a thermometer, an air-introducing tube and baffle plates was charged with 3.89 g (17.4 mmol) of $CuBr_2$, 0.76 g (4.4 mmol) of N,N'-di-t-butylethylenediamine, 23.38 g (231.1 mmol) of n-butyldimethylamine and 2,600 g of toluene. The components were stirred at a reaction temperature of 40° C. A mixed solution was obtained by dissolving 129.32 g (0.48 mol) of HMBP, 292.23 g (2.39 mol) of 2,6-dimethylphenol, 0.51 g (2.9 mmol) of N,N'-di-t-butylethylenediamine and 15.59 g (154.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 23.63 g (52.2 mmol) of tetrasodium ethylenediamine tetraacetate was dissolved was added to the stirred mixture to terminate the reaction. An aqueous layer and an organic layer were separated. Then, the organic layer was washed with pure water, to obtain 2,959.43 g of a reaction solution (B) of a bifunctional phenylene ether oligomer. The bifunctional phenylene ether oligomer had a number average molecular weight of 930, a weight average molecular weight of 1,460 and a hydroxyl group equivalent of 465.

Referential Example 5

A longitudinally long reactor having a volume of 12 liters and equipped with a stirrer, a thermometer, an air-introducing tube and baffle plates was charged with 5.48 g (24.5 mmol) of $CuBr_2$, 1.07 g (6.2 mmol) of N,N'-di-t-butylethylenediamine, 32.93 g (325.4 mmol) of n-butyldimethylamine and 2,600 g of toluene. The components were stirred at a reaction temperature of 40° C. A mixed solution was obtained by dissolving 75.00 g (0.28 mol) of HMBP, 508.44 g (4.16 mol) of 2,6-dimethylphenol, 0.72 g (4.2 mmol) of N,N'-di-t-butylethylenediamine and 21.95 g (217.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 33.29 g (73.6 mmol) of tetrasodium ethylenediamine tetraacetate was dissolved was added to the stirred mixture to terminate the reaction. An aqueous layer and an organic layer were separated. Then, the organic layer was washed with pure water, to obtain 3,121.61 g of a reaction solution (C) of a bifunctional phenylene ether oligomer. The bifunctional phenylene ether oligomer had a number average molecular weight of 2,150, a weight average molecular weight of 3,650 and a hydroxyl group equivalent of 1,050.

Referential Example 6

A longitudinally long reactor having a volume of 12 liters and equipped with a stirrer, a thermometer, an air-introducing tube and baffle plates was charged with 3.89 g (17.4 mmol) of $CuBr_2$, 0.76 g (4.4 mmol) of N,N'-di-t-butylethylenediamine, 23.41 g (231.3 mmol) of n-butyldimethylamine and 2,600 g of toluene. The components were stirred at a reaction temperature of 40° C. A mixed solution was obtained by dissolving 136.03 g (0.48 mol) of 4,4'-(1-methylethylidene)bis(2,6-dimethylphenol), 292.19 g (2.40 mol) of 2,6-dimethylphenol, 0.51 g (3.0 mmol) of N,N'-di-t-butylethylenediamine and 15.61 g (154.2 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 23.66 g (52.3 mmol) of tetrasodium ethylenediamine tetraacetate was dissolved was added to the stirred mixture to terminate the reaction. An aqueous layer and an organic layer were separated. Then, the organic layer was washed with pure water, to obtain 2,969.00 g of a reaction solution (D) of a bifunctional phenylene ether oligomer. The bifunctional phenylene ether oligomer had a number average molecular weight of 940, a weight average molecular weight of 1,490 and a hydroxyl group equivalent of 450.

Referential Example 7

A longitudinally long reactor having a volume of 12 liters and equipped with a stirrer, a thermometer, an air-introducing tube and baffle plates was charged with 3.88 g (17.4 mmol) of $CuBr_2$, 0.76 g (4.4 mmol) of N,N'-di-t-butylethylenediamine, 23.38 g (231.1 mmol) of n-butyldimethylamine and 2,600 g of toluene. The components were stirred at a reaction temperature of 40° C. A mixed solution was obtained by dissolving 129.32 g (0.48 mol) of HMBP, 292.19 g (2.39 mol) of 2,6-dimethylphenol, 0.51 g (2.9 mmol) of N,N'-di-t-butylethylenediamine and 15.59 g (154.0 mmol) of n-butyldimethylamine in 2,300 g of methanol in advance. The mixed solution was dropwise added to the mixture in the reactor over 230 minutes while carrying out bubbling with 5.2 L/min of a nitrogen-air mixed gas having an oxygen concentration of 8%, and stirring was carried out. After the completion of the addition, 1,500 g of water in which 23.63 g (52.2 mmol) of tetrasodium ethylenediamine tetraacetate was dissolved was added to the stirred mixture to terminate the reaction. An aqueous layer and an organic layer were separated. Then, the organic layer was washed with pure water and then concentrated with an evaporator, to obtain 833.53 g of a 50 wt % toluene solution (E) of a bifunctional phenylene ether oligomer. The bifunctional phenylene ether oligomer had a number average molecular weight of 930, a weight average molecular weight of 1,460 and a hydroxyl group equivalent of 465.

Example 5

905 g of N,N-dimethylacetamide was added to 2,829.24 g of the reaction solution (A) obtained in Referential Example 3, and continuous distillation was carried out under conditions of a column diameter of 25 mm, a theoretical column stage number of 15 stages (upper stages 7, lower stages 8), a boiler temperature of 200° C., a feed amount of 200 g/hr and a reflux ratio of 1.10, to obtain 1,118.99 g of a bifunctional phenylene ether oligomer solution (A') containing 74.93% by weight of N,N-dimethylacetamide and 0.10% by weight of toluene. Then, a reactor equipped with a stirrer, a thermometer and a reflux tube was charged with 598.05 g (OH equivalent 0.46 mol) of the bifunctional phenylene ether oligomer solution (A') and 77.15 g (0.51 mol) of chloromethylstyrene (tradename CMS-P; supplied by Seimi Chemical Co., Ltd.), and the mixture was stirred under heat at 50° C. 96.16 g (0.51 mol) of a methanol solution (concentration: 28.4 wt %) of sodium methoxide was dropwise added thereto with retaining the reaction temperature of 50° C. and the resultant mixture was stirred for 1 hour. Further, 8.74 g (0.05 mol) of a methanol solution (same) of sodium methoxide was dropwise added thereto and the resultant mixture was stirred for 2 hours. Then, 5.30 g (0.05 mol) of 85 wt % phosphoric acid aqueous solution was added to the stirred mixture, an inorganic salt generated was removed, and then the reaction solution was dropwise added to a mixed solution of 373 g of water and 373 g of methanol, to obtain a solid. Solid-liquid separation was carried out with a centrifugal separator. Then, the separated solid was washed with 900 g of methanol and then with 900 g of 60° C. hot water. Then, the washed solid was dried under a reduced pressure to obtain 186.46 g of an intended vinyl compound. The vinyl compound was molten, degassed and molded at 150° C. and cured at 200° C. for 3 hours, to obtain a cured product. Table 2 shows analysis results of the vinyl compound and dielectric characteristics of the cured product.

Example 6

1,250 g of N,N-dimethylacetamide was added to 2,959.43 g of the reaction solution (B) obtained in Referential Example 4, and continuous distillation was carried out under the same conditions as those of Example 5, to obtain 1,553.72 g of a bifunctional phenylene ether oligomer solution (B') containing 74.78% by weight of N,N-dimethylacetamide and 0.30% by weight of toluene. Then, a reactor equipped with a stirrer, a thermometer and a reflux tube was charged with 791.15 g (OH equivalent 0.42 mol) of the bifunctional phenylene ether oligomer solution (B') and 71.20 g (0.47 mol) of chloromethyl styrene (CMS-P), and the mixture was stirred under heat at 50° C. 88.71 g (0.47 mol) of a methanol solution (concentration: 28.4 wt %) of sodium methoxide was dropwise added thereto with retaining the reaction temperature of 50° C. and the resultant mixture was stirred for 1 hour. Further, 12.10 g (0.06 mol) of a methanol solution (same) of sodium methoxide was dropwise added thereto and the resultant mixture was stirred for 2 hours. Then, 7.33 g (0.06 mol) of 85 wt % phosphoric acid aqueous solution was added to the stirred mixture, an inorganic salt generated was removed, and then the reaction solution was dropwise added to 890 g of water, to obtain a solid. Solid-liquid separation was carried out with a centrifugal separator. Then, the separated solid was washed with 1,200 g of methanol and then with 1,200 g of pure water. Then, the washed solid was dried under a reduced pressure to obtain 234.32 g of an intended vinyl compound. The vinyl compound was molten, degassed and molded at 150° C. and cured at 200° C. for 3 hours, to obtain a cured product. Table 2 shows analysis results of the vinyl compound and dielectric characteristics of the cured product.

Example 7

1,725 g of N,N-dimethylacetamide was added to 3,121.61 g of the reaction solution (C) obtained in Referential Example 5, and continuous distillation was carried out under the same conditions as those of Example 5, to obtain 2,149.13 g of a bifunctional phenylene ether oligomer solution (C') containing 74.85% by weight of N,N-dimethylacetamide and 0.20% by weight of toluene. Then, a reactor equipped with a stirrer, a thermometer and a reflux tube was charged with 1,034.00 g (OH equivalent 0.25 mol) of the bifunctional phenylene ether oligomer solution (C') and 48.75 g (0.32 mol) of chloromethyl styrene (CMS-P), and the mixture was stirred under heat at 50° C. 60.75 g (0.32 mol) of a methanol solution (concentration: 28.4 wt %) of sodium methoxide was dropwise added thereto with retaining the reaction temperature of 50° C. and the resultant mixture was stirred for 1 hour. Further, 7.01 g (0.04 mol) of a methanol solution (same) of sodium methoxide was dropwise added thereto and the resultant mixture was stirred for 2 hours. Then, 4.25 g (0.04 mol) of 85 wt % phosphoric acid aqueous solution was added to the stirred mixture, an inorganic salt generated was removed, and then the reaction solution was dropwise added to 1,160 g of water, to obtain a solid. Solid-liquid separation was carried out with a centrifugal separator. Then, the separated solid was washed with 1,600 g of methanol and then with 1,600 g of pure water. Then, the washed solid was dried under a reduced pressure to obtain 274.49 g of an intended vinyl compound. The vinyl compound was molten, degassed and molded at 150° C. and cured at 200° C. for 3 hours, to obtain a cured product. Table 2 shows analysis results of the vinyl compound and dielectric characteristics of the cured product.

Example 8

1,251 g of N,N-dimethylformamide was added to 2,969.00 g of the reaction solution (D) obtained in Referential Example 6, and continuous distillation was carried out under the same conditions as those of Example 5, to obtain 1,558.99 g of a bifunctional phenylene ether oligomer solution (D') containing 74.89% by weight of N,N-dimethylformamide and 0.15% by weight of toluene. Then, a reactor equipped with a stirrer, a thermometer and a reflux tube was charged with 788.12 g (OH equivalent 0.44 mol) of the bifunctional phenylene ether oligomer solution (D') and 73.40 g (0.48 mol) of chloromethyl styrene (CMS-P), and the mixture was stirred under heat at 50° C. 91.47 g (0.48 mol) of a methanol solution (concentration: 28.4 wt %) of sodium methoxide was dropwise added thereto with retaining the reaction temperature of 50° C. and the resultant mixture was stirred for 1 hour. Further, 12.47 g (0.07 mol) of a methanol solution (same) of sodium methoxide was dropwise added thereto and the resultant mixture was stirred for 2 hours. Then, 7.56 g (0.07 mol) of 85 wt % phosphoric acid aqueous solution was added to the stirred mixture, an inorganic salt generated was removed, and then the reaction solution was dropwise added to 885 g of water, to obtain a solid. Solid-liquid separation was carried out. Then, the separated solid was washed with 1,200 g of methanol and then with 1,200 g of pure water. Then, the washed solid was dried under a reduced pressure to obtain 232.30 g of an intended vinyl compound. The vinyl compound was molten, degassed and molded at 150° C. and cured at 200° C. for 3 hours, to obtain a cured product. Table 2 shows analysis results of the vinyl compound and dielectric characteristics of the cured product.

Comparative Example 3

A reactor equipped with a stirrer, a thermometer and a reflux tube was charged with 200.0 g (OH equivalent 0.22 mol) of the 50 wt % toluene solution (E) of the bifunctional phenylene ether oligomer obtained in Referential Example 7, 36.1 g (0.24 mol) of chloromethyl styrene (CMS-P) and 300 g of N,N-dimethylacetamide, and the mixture was stirred under heat at 50° C. 45.00 g (0.24 mol) of a methanol solution of sodium methoxide (concentration: 28.4 wt %) was dropwise added thereto with retaining the reaction temperature of 50° C. and the resultant mixture was stirred for 3 hours. Further, 6.14 g (0.03 mol) of a methanol solution of sodium methoxide (same) was dropwise added thereto and the resultant mixture was stirred for 3 hours (since toluene, being a nonpolar solvent which decreased the synthetic reaction rate of a vinyl compound, remained, it took a longer time for unreacted chloromethyl styrene to disappear as compared with Examples). Then, 3.72 g (0.03 mol) of 85 wt % phosphoric acid aqueous solution was added to the stirred mixture, an inorganic salt generated was removed, and then the reaction solution was dropwise added to 450 g of water. In this case, a viscous material was obtained so that solid-liquid separation was difficult.

Comparative Example 4

The same reaction solution, from which an inorganic salt had been removed, as that obtained in Comparative Example 3 was dropwise added to a mixed solution of 2,000 g of methanol and 500 g of water to obtain a solid, and solid-liquid separation was carried out (since the reaction solution contained toluene, a large amount of the water/alcohol mixed solution was required as a poor solvent). Then, the separated solid was washed with 750 g of methanol and then with 750 g of pure water, and the washed solid was dried under a reduced pressure to obtain 112.52 g of an intended vinyl compound. The vinyl compound was molten, degassed and molden at 150° C. and cured at 200° C. for 3 hours, to obtain a cured product. Table 2 shows analysis results of the vinyl compound and dielectric characteristics of the cured product.

Comparative Example 5

A reactor equipped with a stirrer, a thermometer and a reflux tube was charged with 791.30 g (OH equivalent 0.42 mol) of the bifunctional phenylene ether oligomer solution (B') obtained in Example 6 and 71.22 g (0.47 mol) of chloromethyl styrene (CMS-P), and the mixture was stirred under heat at 50° C. 88.73 g (0.47 mol) of a methanol solution (concentration: 28.4 wt %) of sodium methoxide was dropwise added thereto with retaining the reaction temperature of 50° C. and the resultant mixture was stirred for 1 hour. Further, 12.10 g (0.06 mol) of a methanol solution (same) of sodium methoxide was dropwise added thereto and the resultant mixture was stirred for 2 hours. An inorganic salt generated was removed and then the reaction solution was dropwise added to 890 g of water, to obtain a solid. Solid-liquid separation was carried out with a centrifugal separator. Then, the separated solid was washed with 1,200 g of methanol and then with 1,200 g of pure water. Then, the washed solid was dried under a reduced pressure to obtain 235.42 g of an intended vinyl compound. The vinyl compound was molten, degassed and molded at 150° C. and cured at 200° C. for 3 hours, to obtain a cured product. Table 2 shows analysis results of the vinyl compound and dielectric characteristics of the cured product.

TABLE 2

| | | Example 5 | Example 6 | Example 7 | Example 8 | Comparative Example 3 | Comparative Example 4 | Comparative Example 5 |
|---|---|---|---|---|---|---|---|---|
| Synthetic conditions | Reaction solvent | DMAC | DMAC | DMAC | DMF | DMAC/toluene | DMAC/toluene | DMAC |
| | Reaction time[hr] | 3 | 3 | 3 | 3 | 6 | 6 | 3 |
| | Poor solvent for solidification | Methanol water | Water | Water | Water | Water | Methanol Water | Water |
| | Amount of poor solvent for solidification [phr] | 500 | 450 | 450 | 450 | 450 | 2,500 | 450 |
| | Hydrolysable chlorine [ppm] | 80 | 50 | 80 | 50 | — | 80 | 120 |
| Properties of vinyl compound | Number average molecular weight | 850 | 1,210 | 2,300 | 1,205 | — | 1,210 | 1,250 |
| | Weight average molecular weight | 1,260 | 1,820 | 3,840 | 1,810 | — | 1,830 | 1,830 |
| | Na[ppm] | N.D. | N.D. | N.D. | N.D. | — | N.D. | 950 |
| Cured product | Dielectric constant [10 GHz] | 2.4 | 2.38 | 2.36 | 2.4 | — | 2.39 | 2.39 |
| | Dielectric loss tangent [10 GHz] | 0.0027 | 0.0028 | 0.0025 | 0.0031 | — | 0.0032 | 0.0032 |

DMAC: N,N-dimethylacetamide
DMF: N,N-dimethylformamide
N.D.: Not detected
The amount of a poor solvent for solidification was per 100 phr of bifunctional phenylene ether oligomer.

What is claimed is:

1. A process for the production of a vinyl compound of the formula (1),

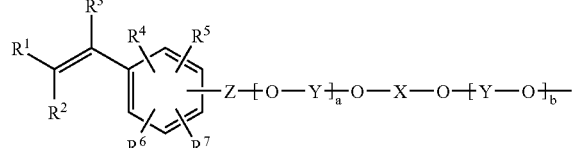

(1)

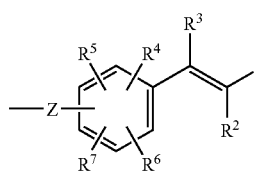

wherein:
$R^1$, $R^2$, $R^3$, $R^4$, $R^5$, $R^6$ and $R^7$ are the same or different and represent a hydrogen atom, a halogen atom, an alkyl group or a phenyl group,
—(O—X—O)— represents a moiety of the formula (3) or the formula (4),

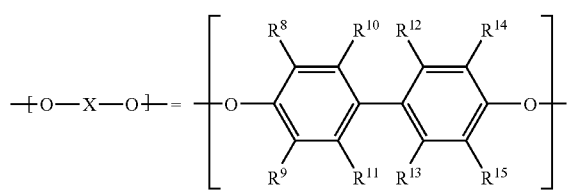

(3)

in which $R^8$, $R^9$, $R^{10}$, $R^{14}$ and $R^{15}$ are the same or different and represent a halogen atom, an alkyl group having 6 or less carbon atoms or a phenyl group and $R^{11}$, $R^{12}$ and $R^{13}$ are the same or different and represent a hydrogen atom, a halogen atom, an alkyl group having 6 or less carbon atoms or a phenyl group,

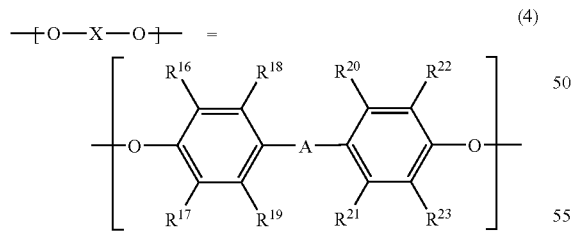

(4)

in which $R^{16}$, $R^{17}$, $R^{22}$ and $R^{23}$ are the same or different and represent a halogen atom, an alkyl group having 6 or less carbon atoms or a phenyl group, $R^{18}$, $R^{19}$, $R^{20}$ and $R^{21}$ are the same or different and represent a hydrogen atom, a halogen atom, an alkyl group having 6 or less carbon atoms or a phenyl group, and A is a linear, branched or cyclic hydrocarbon having 20 or less carbon atoms,
—(Y—O)— is a moiety of the formula (5) or a random arrangement of at least two kinds of moieties of the formula (5),

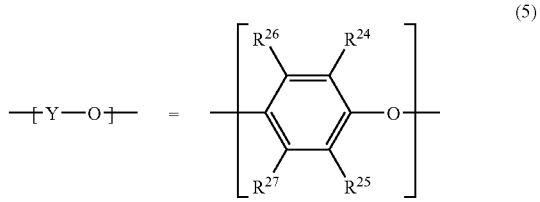

(5)

in which $R^{24}$ and $R^{25}$ are the same or different and represent a halogen atom, an alkyl group having 6 or less carbon atoms or a phenyl group and $R^{26}$ and $R^{27}$ are the same or different and represent a hydrogen atom, a halogen atom, an alkyl group having 6 or less carbon atoms or a phenyl group,
Z is an organic group having at least one carbon atom which may contain an oxygen atom, a nitrogen atom or a sulfur atom, and
each of a and b is an integer of 0 to 30, provided that at least one of a and b is not 0,
which process comprises reacting a bifunctional phenylene ether oligomer of the formula (2) with a vinylbenzyl halide in an aprotic polar solvent in the presence of an alkali metal alkoxide and then adding the reaction solution to a water/alcohol mixed solution to precipitate a solid,

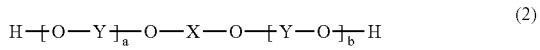

(2)

in which —(O—X—O)—, —(Y—O)—, a and b areas defined in the formula (1).

2. A process according to claim 1,
wherein $R^8$, $R^9$, $R^{10}$, $R^{14}$ and $R^{15}$ in the formula (3) or $R^{16}$, $R^{17}$, $R^{22}$ and $R^{23}$ in the formula (4) are methyl groups and —(Y—O)—, represented by the formula (5), is a moiety of the formula (6) or the formula (7) or a random arrangement of moieties of the formula (6) and the formula (7).

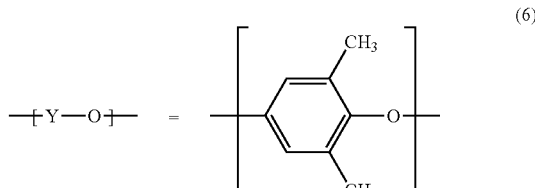

(6)

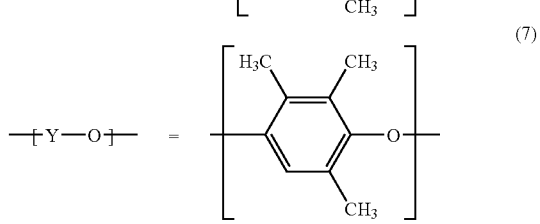

(7)

3. A process according to claim 1,
wherein the vinylbenzyl halide is one member or at least two members selected from the group consisting of m-vinylbenzyl chloride, p-vinylbenzyl chloride and a mixture of these, m-vinylbenzyl bromide, p-vinylbenzyl bromide and a mixture of these.

4. A process according to claim 1,
wherein the alkali metal alkoxide is one member or at least two members selected from the group consisting of lithium methoxide, sodium methoxide, potassium methoxide, lithium ethoxide, sodium ethoxide and potassium ethoxide.

5. A process according to claim 1,
wherein the aprotic polar solvent is one member or at least two members selected from the group consisting of acetone, methyl ethyl ketone, methyl isobutyl ketone, N,N-dimethylformamide, N,N-dimethylacetamide and N-methyl-2-pyrolidone.

6. A process according to claim 1,
wherein the alcohol of the water/alcohol mixed solution is one member or at least two members selected from the group consisting of methanol, ethanol, propanol and isopropanol.

7. A process for the production of a vinyl compound of the formula (1),

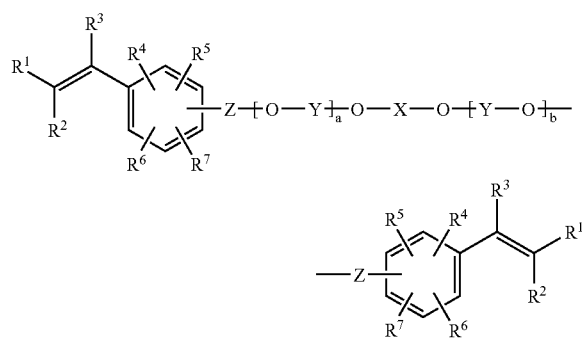

wherein:
$R^1$, $R^2$, $R^3$, $R^4$, $R^5$, $R^6$ and $R^7$ are the same or different and represent a hydrogen atom, a halogen atom, an alkyl group or a phenyl group,
—(O—X—O)— represents a moiety of the formula (3) or the formula (4),

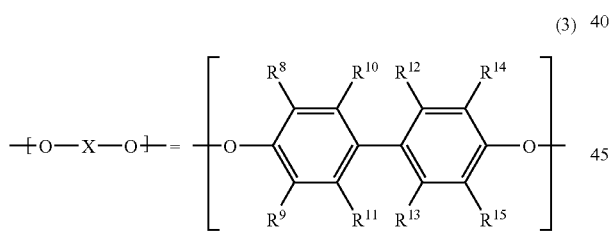

in which $R^8$, $R^9$, $R^{10}$, $R^{14}$ and $R^{15}$ are the same or different and represent a halogen atom, an alkyl group having 6 or less carbon atoms or a phenyl group and $R^{11}$, $R^{12}$ and $R^{13}$ are the same or different and represent a hydrogen atom, a halogen atom, an alkyl group having 6 or less carbon atoms or a phenyl group,

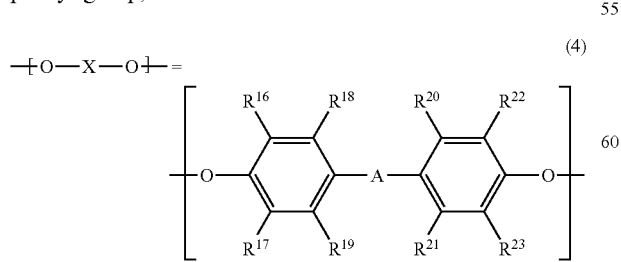

in which $R^{16}$, $R^{17}$, $R^{22}$ and $R^{23}$ are the same or different and represent a halogen atom, an alkyl group having 6 or less carbon atoms or a phenyl group, $R^{18}$, $R^{19}$, $R^{20}$ and $R^{21}$ are the same or different and represent a hydrogen atom, a halogen atom, an alkyl group having 6 or less carbon atoms or a phenyl group, and A is a linear, branched or cyclic hydrocarbon having 20 or less carbon atoms,
—(Y—O)— is a moiety of the formula (5) or a random arrangement of at least two kinds of moieties of the formula (5),

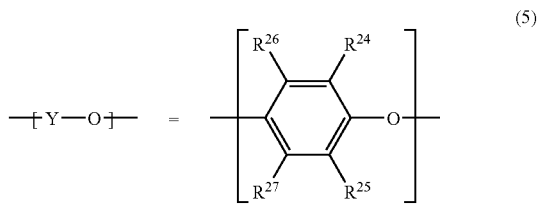

in which $R^{24}$ and $R^{25}$ are the same or different and represent a halogen atom, an alkyl group having 6 or less carbon atoms or a phenyl group and $R^{26}$ and $R^{27}$ are the same or different and represent a hydrogen atom, a halogen atom, an alkyl group having 6 or less carbon atoms or a phenyl group,
Z is an organic group having at least one carbon atom which may contain an oxygen atom, a nitrogen atom or a sulfur atom, and
each of a and b is an integer of 0 to 30, provided that at least one of a and b is not 0,
which process comprises adding an aprotic polar solvent having a boiling point higher than that of a reaction solvent of a reaction solution (a) which has synthesized a bifunctional phenylene ether oligomer of the formula (2) to the reaction solution (a), replacing the reaction solvent of the reaction solution (a) with the aprotic polar solvent by distillation to obtain a bifunctional phenylene ether oligomer solution, reacting the bifunctional phenylene ether oligomer solution with a vinylbenzyl halide in the presence of an alkali metal alkoxide to synthesize the vinyl compound of the formula (1) and obtain a reaction solution (b), neutralizing the reaction solution (b) with an acid substance and then adding the neutralized solution to water or a water/alcohol mixed solution, to precipitate a solid,

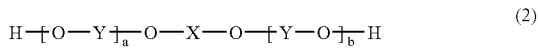

in which —(O—X—O)—, —(Y—O)—, a and b areas defined in the formula (1).

8. A process according to claim 7,
wherein the content of the reaction solvent for the synthesis of the bifunctional phenylene ether oligomer in the bifunctional phenylene ether oligomer solution replaced with the aprotic polar solvent is 5% by weight or less.

9. A process according to claim 7,
wherein the aprotic polar solvent is one member or at least two members selected from the group consisting of N,N-dimethylformamide, N,N-dimethylacetamide and N-methyl-2-pyrrolidone.

10. A process according to claim 7,
wherein the acid substance is one member or at least two members selected from the group consisting of phosphoric acid, sulfuric acid, aromatic sulfonic acid and and aromatic carboxylic acid.

* * * * *